(12) United States Patent
Murphy

(10) Patent No.: US 7,998,220 B2
(45) Date of Patent: Aug. 16, 2011

(54) METHODS FOR TREATING OBESITY

(76) Inventor: Timothy P. Murphy, Providence, RI (US)

( * ) Notice: Subject to any disclaimer, the term of this patent is extended or adjusted under 35 U.S.C. 154(b) by 1582 days.

(21) Appl. No.: 10/770,403

(22) Filed: Feb. 4, 2004

(65) Prior Publication Data

US 2005/0171556 A1 Aug. 4, 2005

(51) Int. Cl.
*A61F 2/04* (2006.01)
(52) U.S. Cl. .................................. 623/23.64
(58) Field of Classification Search .............. 623/1.31, 623/23.64; 128/898; 606/158; 607/40
See application file for complete search history.

(56) References Cited

U.S. PATENT DOCUMENTS

| | | | | |
|---|---|---|---|---|
| 3,730,186 A | * | 5/1973 | Edmunds et al. | 606/158 |
| 5,618,301 A | | 4/1997 | Hauenstein et al. | 606/198 |
| 5,690,644 A | * | 11/1997 | Yurek et al. | 623/1.11 |
| 6,120,534 A | * | 9/2000 | Ruiz | 623/1.19 |
| 6,953,476 B1 | * | 10/2005 | Shalev | 623/1.15 |
| 2002/0161414 A1 | * | 10/2002 | Flesler et al. | 607/40 |
| 2003/0105332 A1 | * | 6/2003 | Booth et al. | 546/339 |
| 2005/0055082 A1 | * | 3/2005 | Ben Muvhar et al. | 623/1.15 |

* cited by examiner

*Primary Examiner* — Paul Prebilic
(74) *Attorney, Agent, or Firm* — Cermak Nakajima LLP; Adam J. Cermak

(57) ABSTRACT

A system and methods useful for treating morbid obesity include the installation of a stenosis into an artery of a morbidly obese patient, the artery selected to be one that supplies blood to the small intestine of the patient.

15 Claims, 3 Drawing Sheets

METHODS FOR TREATING OBESITY

BACKGROUND OF THE INVENTION

1. Field of the Invention

The present invention relates to devices, systems, and processes useful to treat obesity in patients, and more specifically to the treatment of the morbidly obese.

2. Brief Description of the Related Art

According to the Centers for Disease Control (CDC), the United States is in the midst of an epidemic of obesity (Mokdad A H, Serdula M K, Dietz W H, Bowman B A, Marks J S, Koplan J P, "The spread of the obesity epidemic in the United States 1991-1998", JAMA 1999; 282: 1519-22). More than half of the U.S. population is overweight. One third of it is classified as obese, with more than 5 million adults in the U.S. having a body mass index>40 (BMI=weight in kg/height in meters). Ten million more are near that mark and may be at risk for obesity-related health problems. The problem is increasing; obesity in children and adolescents increased two-fold in the last decades. Obesity is associated with increased cardiovascular disease risk (Mokdad A H, Ford E S, Bowman B A, Dietz W H, Vinicor F, Bales V S, et al, "Prevalence of obesity, diabetes, and obesity-related health risk factors, 2001", JAMA 2003; 289: 76-9) and mortality (Fontaine K R, Redden D T, Wang C, Westfall A O, Allison D B, "Years of life lost due to obesity", JAMA 2003; 289: 187-93; Crespo C J, Palmieri M R, Perdomo R P, Mcgee D L, Smit E, Sempos C T., et al., "The relationship of physical activity and body weight with all-cause mortality: results from the Puerto Rico Heart Health Program", Ann. Epidemiol. 2002; 12: 543-52). According to the Social Security Administration (SSA), $77 million are paid monthly to approximately 137,000 persons who meet obesity requirements for disability.

After smoking, obesity is the second most preventable disease causing death. Approximately 300,000 Americans die every year, and millions more suffer, due to obesity-related co-morbidities. These include, but are not limited to, hypertension, cardiac disease, dyslipidemia, diabetes mellitus type 2, stroke, sleep apnea and other respiratory disorders, arthritis of weight-bearing joints, gallbladder disease, gastroesophageal reflux, stress urinary incontinence, infertility and hormonal imbalances, skin disorders, and some types of cancer.

Depression, low self-esteem, societal rejection and prejudice, lesser work and income opportunities, marital, familiar, social and sexual problems add to the burden of the morbidly obese. Approximately $100 billion is spent annually in the United States for the treatment of these obesity-related diseases. An almost equal amount is spent yearly in diets and low-calorie foods and drinks, exercise programs and other weight loss treatments which, even if successful, offer only temporary relief.

There are ten times as many candidates for obesity surgery in the U.S. as for heart bypass surgery annually. The American Society of Bariatric Surgery has only 500 members who perform gastric-bypass operations. Waiting lists are months long.

Several surgical methods have been tried to help those with morbid obesity to lose weight. Various small bowel and stomach operations were tried. Often, these attempts had high complication rates and did not result in significant weight loss. The currently used surgical method of bariatric surgery involves surgical separation of the majority of the stomach from the intestinal tract, and stapling of the gastric remnant to allow very little capacity to store food. The small intestine is anastomosed to the stomach, and the gastric contents empty directly into the jejunum, bypassing the duodenum. Although initially people who undergo this operation may have symptoms associated with eating, usually their appetite gradually decreases for poorly understood reasons. Because of the frequency of morbid obesity in our population, the demand for this operation greatly exceeds the supply. There may be as many as 2 million people in the U.S. who would be candidates for this operation. Most practitioners who offer this procedure are booked many months ahead and can't keep up with the demand. It is likely that one day this will be one of the most frequently performed operations, and exceed the volume of coronary artery bypass graft procedures (250,000 cases/year).

Despite being performed in patients often in their 20's or 30's, the surgery is associated with substantial morbidity and an approximately 1% death rate. Patients with morbid obesity are not ideal for major abdominal surgery. Major complications are observed in 20% of patients, and death occurs in 0.3-1%. This is tragic because often the patients are very young. Additionally, significant permanent weight loss occurs in only 80%.

Weight loss, on the other hand, is sometimes associated with an uncommon vascular condition, chronic mesenteric ischemia. Patients with chronic mesenteric ischemia have blockages in arteries that supply the gut. While they have enough blood flow to keep the small intestine alive at rest, they can't achieve the 3-fold increase in blood flow required after eating for the intestine to fully function. They experience abdominal pain after eating, often accompanied by weight loss and diarrhea after eating. They adapt their eating to avoid these symptoms, namely by eating small amounts frequently. After a while, their appetites are decreased and they no longer crave food. For example, there are some adult patients with mesenteric ischemia who weigh 80 pounds and are cachectic, but are not hungry.

Patients with chronic mesenteric ischemia are usually older and classically have atherosclerotic stenosis or occlusion of all three arteries supplying the bowel, including the celiac axis, the superior mesenteric artery, and the inferior mesenteric artery. However, when collaterals are not well-developed, patients can be symptomatic with involvement of only the artery that supplies the small bowel, the superior mesenteric artery.

SUMMARY OF THE INVENTION

One aspect of the present invention includes a method of treating morbid obesity in a patient comprising reducing mesenteric blood flow, duodenal blood flow, jejunal blood flow, ileal blood flow, or combinations thereof, in the patient.

Another aspect of the present invention includes an endograft comprising a hollow first portion configured and arranged to be self-expanding, and a hollow second portion attached to the first portion configured and arranged to be expandable and to maintain a shape.

BRIEF DESCRIPTION OF THE DRAWINGS

The invention of the present application will now be described in more detail with reference to preferred embodiments of the apparatus and method, given only by way of example, and with reference to the accompanying drawings, in which.

DETAILED DESCRIPTION OF THE PREFERRED EMBODIMENTS

Figure 1:
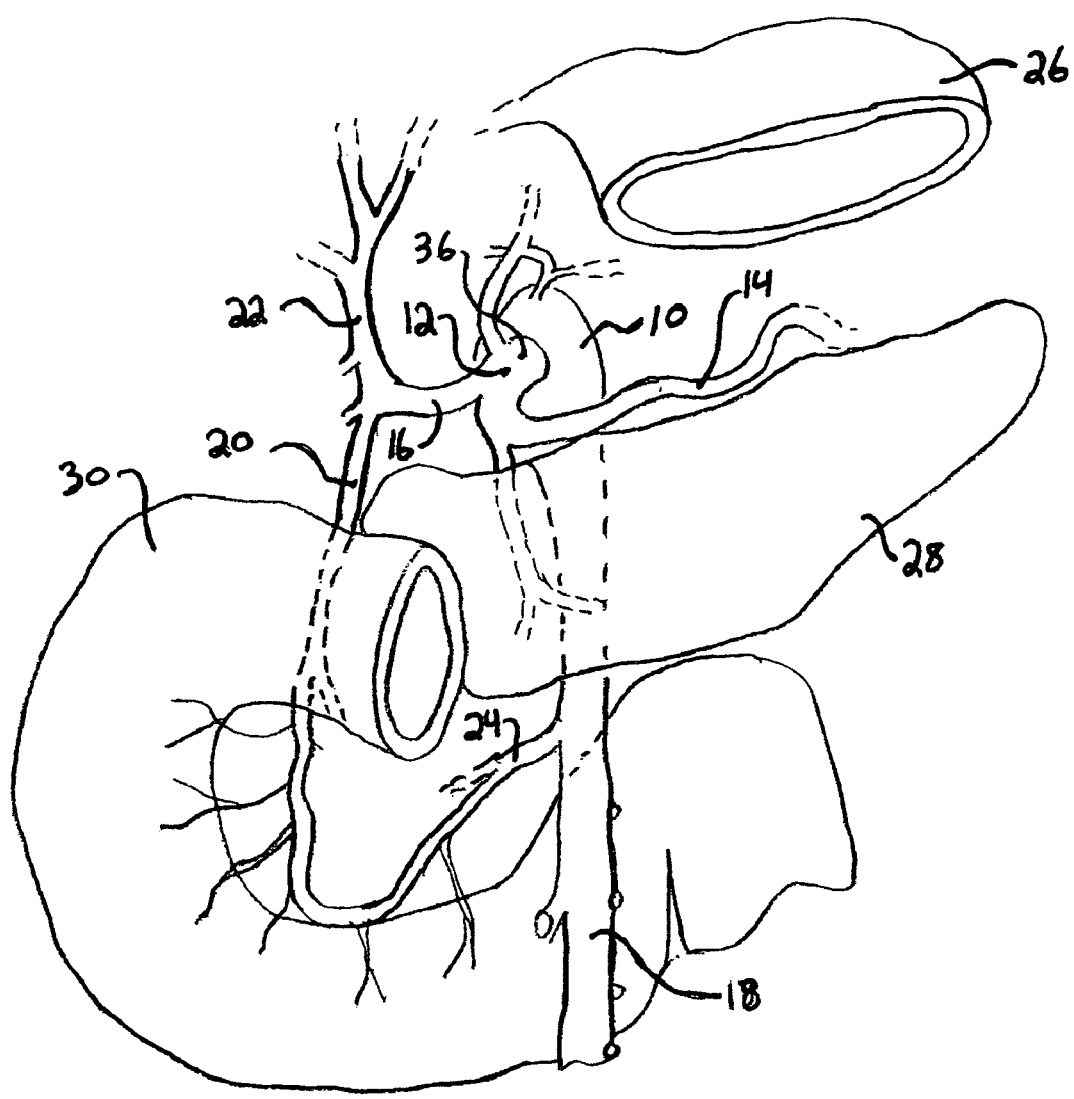
FIG. 1 illustrates some of the internal organs and arteries in the human gut.

Referring to the drawing figures, like reference numerals designate identical or corresponding elements throughout the several figures.

Aspects and attendant advantages of the present invention will become apparent to those skilled in the art from a reading of the following detailed description of embodiments constructed in accordance therewith, taken in conjunction with the accompanying drawings.

One aspect of the present invention is that obesity can be affected by vascular procedures because weight loss is associated with chronic mesenteric ischemia. Thus, another aspect of the present invention includes percutaneous transluminal treatment options for morbid obesity. More particularly, an aspect of the present invention includes placing a narrowing, partial blockage, stenosis, or blood-flow restrictor into an artery that supplies blood to the duodenum, the lower intestine, jejunum, ileum, or combinations thereof. A particularly preferred artery is the superior mesenteric artery, although the present invention is not limited to treatment of a patient by reducing blood flow through this vessel, or to reducing blood flow in a single artery. By way of example and not of limitation, the blood flow through arteries that are collateral to the superior mesenteric artery, e.g., the gastroduodenal and inferior mesenteric arteries, is optionally also reduced, so that collateral blood flow does not make up for the blood flow reductions in the superior mesenteric artery.

While these organs typically have more than one blood supply, restriction of the blood supply by forming a partial blockage in one or more select arteries can induce mesenteric ischemia, thus reducing the effectiveness of the organ to digest food, and consequently reducing the patient's intake of compounds from the food the patient has ingested.

In general terms, another aspect of the present invention includes an endograft with a variable and adjustable central diameter. The endograft preferably has an hourglass shape, that is, narrower in the middle than at the ends. The endograft preferably includes at least two, and more preferably three segments, each of a metallic framework covered by fabric. When provided, the two segments of framework at the ends of the endograft include a self-expandable elastic metal (e.g., Nitinol or Elgiloy), whereas the central framework is formed of an inelastic metal (e.g., 316L stainless steel).

Another aspect of the present invention includes methods useful for treating morbid obesity in a patient. An endograft, such as those described herein, is introduced into the patient's body in an introducer, covered by a sleeve. When in position in the artery of choice that supplies blood to the intestine, the sleeve is retracted and the two self-expanding ends of the endograft expand, fixing the endograft within the artery. Subsequently, the diameter of the middle segment optionally can be dilated to an appropriate larger size with a dilatation device, e.g., an angioplasty balloon or expanding cage dilator, which is positioned in the endograft.

According to a more preferred embodiment, an endograft in accordance with the present invention has a relatively large diameter (approximately 7-8 mm) at its ends, but be tapered centrally like an hourglass, and will be relatively short, e.g. approximately 3-5 cm long. The stenosis formed by the smaller internal diameter in the center of the endograft is highly restrictive of flow, e.g., is about 2 mm in inner diameter. Yet another aspect of the present invention includes forming the narrowing of the central portion of the endograft by dilating the central portion serially as needed to larger diameters, up to, e.g., about 6 mm.

Yet another aspect of the present invention includes that the endograft has a metal self-expanding frame covered with thin polytetrafluoroethylene (PTFE) coating. The endograft is preferably introduced through a 10 French or smaller introducer.

Figure 2:
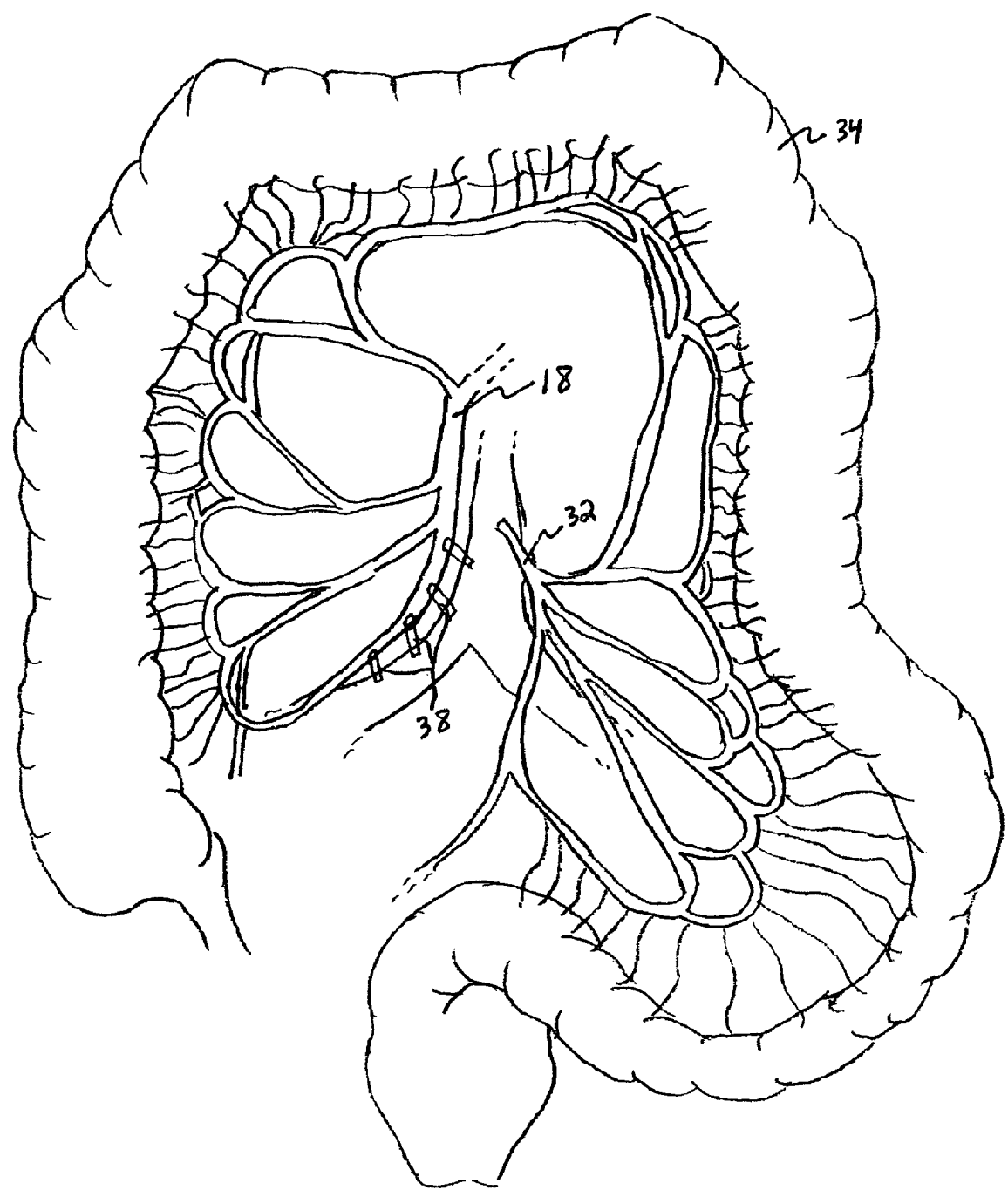
FIG. 2 illustrates other internal organs and arteries in the human gut.

Turning now to the drawing figures, FIGS. 1 and 2 illustrate some of the internal organs and arteries of the human gut. While the present invention is preferably directed to the treatment of morbid obesity in human patients, those of ordinary skill in the art will immediately recognize that the invention is not so limited, and extends to the treatment of other diseases, organ systems, or animal species.

Figure 3:
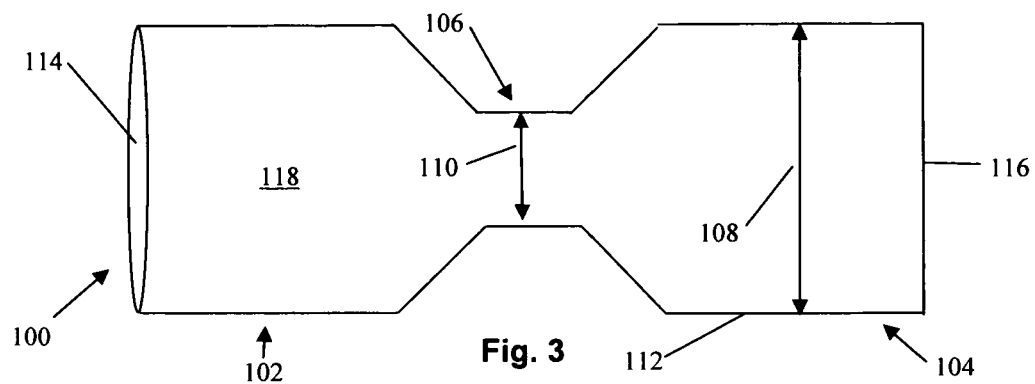
FIG. 3 schematically illustrates a first exemplary embodiment of a device in accordance with the present invention.

The following anatomical features are indicated in FIGS. 1 and 2 to assist in a better understanding of the present invention:

10: abdominal aorta
 12: celiac trunk
 14: splenic artery
 16: common hepatic artery
 18: superior mesenteric artery
 20: gastroduodenal artery
 22: hepatic artery proper
 24: inferior pancreaticoduodenal artery
 26: stomach (portions cut away)
 28: pancreas
 30: duodenum
 32: inferior mesenteric artery
 34: large intestine
 36: celiac axis
 38: jejunal and ileal (intestinal) arteries FIG. 3 illustrates an exemplary embodiment of an endograft device 100 useful to partially occlude a blood vessel, preferably an artery, of choice. The endograft 100 includes at least a first end section 102 and a central section 106, and preferably includes a second end section 104 opposite the first end section. As described above, the end section (s) 102, 104 are formed of a material and/or a framework which will expand racially outwardly if not constrained, and operate to anchor the endograft in position in the artery. One aspect of the present invention includes that the central section 106 is formed of a material and/or a framework that can be radially expanded upon the application of a force radially outward on the section, and that otherwise maintains its shape. In this manner, the inner diameter 108 of the end section(s) 102, 104 has an upper limit that can be larger than the inner diameter 110 of the center section 106. Those of ordinary skill in the art are well acquainted with the numerous self-expanding and expandable framework structures both previously proposed and currently available, and therefore further elaboration on these elements will not be includes so as not to obscure the present invention.

Another, alternative aspect of the present invention includes that the center section 106 is formed of a material that narrows over time. Non-limiting examples of such an alternative center section 106 includes forming the center section of a swellable material that imbibes a fluid, e.g., water, from the blood and increases in size. Thus, when initially positioned in the blood vessel, the center section 106 has a first larger inner diameter, and a second, smaller inner diameter upon absorbing fluid and swelling. Further optionally, a center section 106 in accordance with the present invention can include both swellable and expandable materials.

The endograft 100 is constructed to be disrupt the fluid dynamic of the artery in which the endograft is installed, and is more preferably constructed to be fluid impervious so that blood flowing through the artery must flow into one of the openings 114, 116, and through the lumen 118 of the endograft, and will not pass through any openings or holes (not illustrated) that may be present in the structure(s) from which the end and center sections are constructed. Less preferably, however, the endograft 100 can be constructed to not be fluid impervious, yet can disrupt the laminar flow of the artery sufficiently to impede blood flow. Thus, one aspect of the present invention includes that a layer 112 of a fluid impervious material is included on the exterior, on the interior, incorporated into the framework(s) themselves, or combinations thereof, of the endograft 110. By way of example and not of limitation, the material out of which the layer 112 is formed can be polytetrafluoroethylene (PTFE); those of skill in the art will readily identify other suitable biocompatible, fluid impervious materials for the layer 112 upon a reading of the present disclosure.

With continued reference to FIG. 3, and with additional reference to FIGS. 1, 2, and 4a-4c, yet further aspects of the present invention will now be described. In order to accomplish arterial blood flow reduction to the small intestine, it is another optional aspect of the present invention to occlude the gastroduodenal artery and/or the inferior mesenteric artery of the patient.

Thus, another aspect of the present invention includes that a transluminal, preferably percutaneous, route is selected along which to advance a blood flow reducing device into the artery of choice, to reduce the arterial blood supply to the small intestine. While more preferred aspects of the present invention include positioning an endograft within the lumen of the selected artery, another aspect of the present invention includes injecting an embolic agent or coil into the artery's lumen to reduce the blood flow cross section, e.g., by a transluminal route or injecting through the artery wall. Suitable embolic agents and coils are well known to those of ordinary skill in the art, and the present invention is not limited to any particular embolic agent or coil.

Yet another aspect of the present invention includes other the use of other routes, including but not limited to, open cavity and laparoscopic routes, that can be used to install the endograft. When selecting a route which is not transluminal, partial occlusion can be achieved by open surgical banding, partial clamping, or ligature of the artery of interest to reduce their blood flow. As the devices and tools used in laparoscopic and open surgery are well know to those of ordinary skill in the art, including arterial clamps, bands, and the devices that apply them, further description thereof will not be included here so as not to obscure the present invention. While somewhat less preferred, these are additional aspects of the present invention.

Access is made to the patient's arterial vasculature, e.g., by a standard cut-down, Seldinger, or other process well known to those of skill in the art. Preferably, the patient is one who suffers from morbid obesity. A blood flow reduction device, which may be an endograft 100 such as that illustrated in FIG. 3, is advanced through the patient's vasculature to a point in the artery A of choice where blood flow is to be reduced. As a matter of convenience, reference hereinafter will be made to the endograft 100 as the blood flow reduction device, although the present invention is not restricted to this particular embodiment of a blood flow reduction device.

To facilitate the advancement of the endograft 100, a system can be provided to move the endograft through the vasculature. By way of example and not of limitation, one aspect of the present invention includes the provision of an elongated, hollow sheath 120 and an elongated introducer 122, sized and constructed so that the introducer can fit within the lumen of the sheath and the endograft can be carried in the distal end of the sheath with the introducer positioned proximally thereof. A guidewire (not illustrated) can also be provided to further assist in navigating through the patient's vasculature to reach the point of interest in the artery A of choice. During this period, the end section(s) 102, 104 of the endograft 100, because of their natural tendency to expand radially outwardly, assist in holding the endograft inside the lumen of the sheath 120.

Once the point of interest in the artery A has been reached, the sheath 120 is retracted while the endograft and introducer are held in position relative to the artery. The endograft 100 is thus effectively deployed out of the distal end of the sheath 120 by the introducer 122. Because the end section(s) 102, 104 are constructed to radially expand without further action, the end sections expand to bear against the inner surface of the artery A and to preferably substantially, and more preferably entirely, redirect the flow of blood in the artery through the lumen of the endograft 100. Because the center section 106 of the endograft 100 has a small inner diameter, or more generally a smaller flow cross section regardless of its cross-sectional shape, the blood flow through the artery A is reduced by the endograft 100. As discussed above, a reduction in the blood flow through one of the arteries identified above can induce mesenteric ischemia in the patient, which is known to result in weight loss by the patient.

Figure 4A:
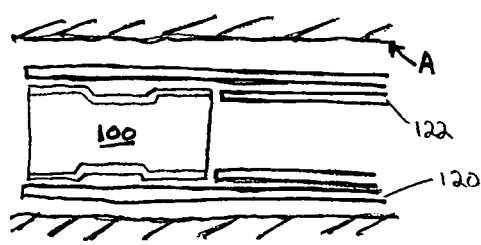
FIGS. 4a-4c schematically illustrate several exemplary steps of an embodiment of a method, as well as additional exemplary devices, in accordance with the present invention.
Figure 4B:
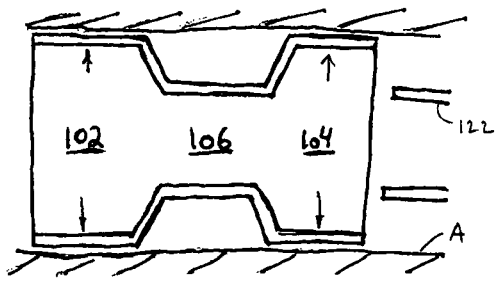
Figure 4C:
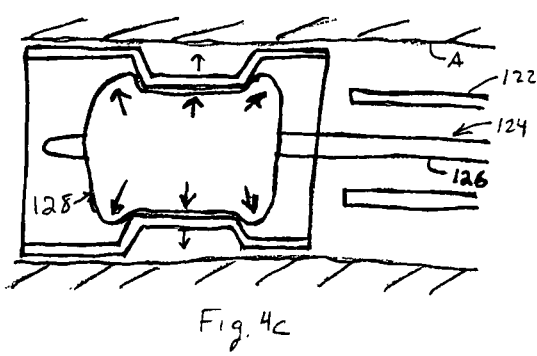

FIG. 4c illustrates yet another aspect of the present invention, the provision of an optional device which cooperates with the other structures already described to permit the medical practitioner to radially expand the center section 106 of the endograft 100, to increase the flow cross-section of the endograft and thus increase the blood flow through the artery. Non-limiting examples of such a device include, but are not limited to, a dilatation balloon catheter, e.g., an angioplasty balloon catheter or vascular stent deployment balloon catheter, and an expanding cage vascular dilator. Those of ordinary skill in the art will readily identify other devices suitable for radially expanding the center section 106 upon a reading of the present disclosure.

Turning back to FIG. 4c, a dilatation balloon catheter 124 includes a hollow shaft 126 on which is mounted a dilatation balloon 128, in a known manner. As will be readily appreciated by those of skill in the art, the catheter 124 can be used in conjunction with the sheath 120 to deploy the endograft 100, and the introducer 122 can therefore be eliminated from the system, if desired. In this case, when the sheath 120 is retracted proximally, the catheter 124 is held in position relative to the artery A, while inflated sufficiently to cause the endograft to slide out the distal end of the sheath. Thus deployed, the catheter 124 (or other dilation device), can be actuated in a known manner to radially expand the balloon 128, which bears on the inner surface of the center section 106 of the endograft 100. With the application of additional radial force on the center section 106, the center section radially expands until a desired flow cross section is achieved. Because the center section 106 is constructed to be both radially expandable and to maintain its shape once expanded, the balloon 128 can then be deflated and the catheter 124 retracted proximally, leaving the endograft 100 in place in the artery A. The endograft 100 acts as a blood flow reduction device, or stenosis, in the artery, which can result in weight loss by the patient.

The patient can be observed for symptoms of abdominal pain at rest and the central, narrowed portion of the endograft 100 can be dilated as needed, nearly up to the full diameter of the end portions, to adjust the pressure change across the endograft to within a desired range, increase blood flow, and reduce the pain. Because meals result in an increase in the blood flow through the arteries discussed herein, an aspect of the present invention includes adjusting the blood flow through one or more of these arteries to relieve non-meal related abdominal pain, while still restricting the blood flow increases that accompany means and causing relative ischemia of the small intestine after eating. This procedure can be performed acutely in the periprocedure or much later, e.g., years after the endograft has been installed.

As mentioned above, the endograft 100 can include only a single end 102 or 104, with the endograft oriented in the artery A with the one end upstream of the center section 106 when installed.

Yet another aspect of the present invention includes that the blood flow reduction device is not permanently installed in the artery A, but instead is either removed after the desired weight loss is achieved, or dissolves slowly in the blood. For an embodiment of the present invention in which the device dissolves, the device is formed of materials which are biocompatible and bioresorbable or are naturally broken down in the blood; such materials are readily available and well known to those or ordinary skill in the art.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

I claim:

1. A method of treating morbid obesity in a patient comprising:
    reducing gastric blood flow, duodenal blood flow, mesenteric blood flow, jejunal blood flow, ileal blood flow, or combinations thereof, in the patient, including placing a blood flow reducing device inside an artery that carries blood to the small intestine.

2. A method in accordance with claim 1, wherein placing comprises placing the blood flow reducing device inside an artery selected from the group consisting of the superior mesenteric artery, the inferior mesenteric artery, and both.

3. A method in accordance with claim 2, wherein the blood flow reducing device comprises an endograft positioned inside the artery.

4. A method in accordance with claim 1, wherein said artery that carries blood to the small intestine is the gastroduodenal artery.

5. A method in accordance with claim 4, wherein the blood flow reducing device comprises an endograft positioned inside the artery.

6. A method in accordance with claim 1, wherein said artery that carries blood to the small intestine is the superior mesenteric artery.

7. A method in accordance with claim 6, wherein the blood flow reducing device comprises an endograft positioned inside the artery.

8. A method in accordance with claim 1, wherein placing comprises placing an endograft inside the artery, the endograft including a first portion having a size selected to hold the endograft in place in the artery, and a second portion smaller than the first portion that reduces blood flow through the artery.

9. A method in accordance with claim 8, further comprising:
    moving a sleeve surrounding the endograft through the artery; and
    wherein placing comprises deploying the endograft from within the sleeve into the artery.

10. A method in accordance with claim 8, further comprising:
    expanding the second portion of the endograft to increase the blood flow rate through the artery.

11. A method in accordance with claim 8, wherein said second portion includes a swellable material.

12. A method in accordance with claim 8, further comprising:
    adjusting the second portion of the endograft to achieve a pressure change within a desired range so that abdominal pain not related to meals does not occur.

13. A method of treating morbid obesity in a patient comprising:
    permanently reducing gastric blood flow, duodenal blood flow, mesenteric blood flow, jejunal blood flow, ileal blood flow, or combinations thereof, in the patient.

14. A method of treating morbid obesity in a patient comprising:
    reducing gastric blood flow, duodenal blood flow, mesenteric blood flow, jejunal blood flow, ileal blood flow, or combinations thereof, a fixed, invariable amount in the patient.

15. A method of treating morbid obesity in a patient comprising:
    continuously reducing gastric blood flow, duodenal blood flow, mesenteric blood flow, jejunal blood flow, ileal blood flow, or combinations thereof, in the patient for a time effective to reduce the patient's weight.

* * * * *